US008026088B2

(12) United States Patent
Yang

(10) Patent No.: US 8,026,088 B2
(45) Date of Patent: Sep. 27, 2011

(54) ANGIOGENIC TYROSYL TRNA SYNTHETASE COMPOSITIONS AND METHODS

(75) Inventor: Xiang-Lei Yang, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 553 days.

(21) Appl. No.: 12/085,884

(22) PCT Filed: Dec. 1, 2006

(86) PCT No.: PCT/US2006/046106
§ 371 (c)(1),
(2), (4) Date: Jun. 2, 2008

(87) PCT Pub. No.: WO2007/064941
PCT Pub. Date: Jun. 7, 2007

(65) Prior Publication Data
US 2009/0110672 A1    Apr. 30, 2009

Related U.S. Application Data

(60) Provisional application No. 60/741,580, filed on Dec. 2, 2005.

(51) Int. Cl.
*C12P 21/06* (2006.01)
*C12N 9/00* (2006.01)
*C12N 1/20* (2006.01)
*C12N 15/00* (2006.01)
*C07H 21/04* (2006.01)

(52) U.S. Cl. .................. 435/183; 435/69.1; 435/252.3; 435/320.1; 536/23.2

(58) Field of Classification Search .................. None
See application file for complete search history.

(56) References Cited

FOREIGN PATENT DOCUMENTS
WO   WO 01/75078   * 10/2001
WO   WO 03/080648  * 10/2003

OTHER PUBLICATIONS

Accession Q9VV60. Published May 1, 2000.*
Accession Q9VV60, published May 1, 2000.*
Yang et al. Trends Biochem Sci. May 2004;29(5):250-6.*

* cited by examiner

*Primary Examiner* — Christian Fronda
(74) *Attorney, Agent, or Firm* — Olson & Cepuritis, Ltd.

(57) ABSTRACT

The present invention provides an isolated tyrosyl tRNA synthetase (TyrRS) polypeptide variant which comprises (a) a Rossmann fold region or a portion thereof, preferably including an 5 coil; and (b) an anticodon recognition domain or portion thereof, preferably including an 14 coil. Preferably, the 5 coil and the 14 coil have a greater spatial separation in the tertiary structure of the variant compared to the corresponding spatial separation in native human TyrRS. The variant preferably comprises an amino acid residue sequence identity of at least about 50% compared to the amino acid residue sequence of human TyrRS (SEQ ID NO: 3), includes at least one non-conservative amino acid residue sequence of human TyrRS, and preferably presents an exposed ELR motif in the 5 coil on an external portion of the tertiary structure of the polypeptide. A preferred TyrRS protein variant comprises the amino acid residue sequence of SEQ ID NO: 4 or a portion thereof. The proteins and protein fragments of the invention are angiogenic and are useful for stimulating angiogenesis in mammalian tissues.

6 Claims, 8 Drawing Sheets

SEQ ID NO: 3
```
  1 MGDAPSPEEK LHLITRNLQE VLGEEKLKEI LKERELKIYW GTATTGKPHV AYFVPMSKIA
 61 DFLKAGCEVT ILFADLHAYL DNMKAPWELL ELRVSYYENV IKAMLESIGV PLEKLKFIKG
121 TDYQLSKEYT LDVYRLSSVV TQHDSKKAGA EVVKQVEHPL LSGLLYPGLQ ALDEEYLKVD
181 AQFGGIDQRK IFTFAEKYLP ALGYSKRVHL MNPMVPGLTG SKMSSSEEES KIDLLDRKED
241 VKKKLKKAFC EPGNVENNGV LSFIKHVLFP LKSEFVILRD EKWGGNKTYT AYVDLEKDFA
301 AEVVHPGDLK NSVEVALNKL LDPIREKFNT PALKKLASAA YPDPSKQKPM AKGPAKNSEP
361 EEVIPSRLDI RVGKIITVEK HPDADSLYVE KIDVGEAEPR TVVSGLVQFV PKEELQDRLV
421 VVLCNLKPQK MRGVESQGML LCASIEGINR QVEPLDPPAG SAPGEHVFVK GYEKGQPDEE
481 LKPKKKVFEK LQADFKISEE CIAQWKQTNF MTKLGSISCK SLKGGNIS
```

Figure 1.

SEQ ID NO: 4
```
  1 MGDAPSPEEK LHLITRNLQE VLGEEKLKEI LKERELKIYW GTATTGKPHV AYFVPMSKIA
 61 DFLKAGCEVT ILFADLHAYL DNMKAPWELL ELRVSYYENV IKAMLESIGV PLEKLKFIKG
121 TDYQLSKEYT LDVYRLSSVV TQHDSKKAGA EVVKQVEHPL LSGLLYPGLQ ALDEEYLKVD
181 AQFGGIDQRK IFTFAEKYLP ALGYSKRVHL MNPMVPGLTG SKMSSSEEES KIDLLDRKED
241 VKKKLKKAFC EPGNVENNGV LSFIKHVLFP LKSEFVILRD EKWGGNKTYT AYVDLEKDFA
301 AEVVHPGDLK NSVEVALNKL LDPIREKFNT PALKKLASAA XPDPSKQKPM AKGPAKNSEP
361 EEVIPSRLDI RVGKIITVEK HPDADSLYVE KIDVGEAEPR TVVSGLVQFV PKEELQDRLV
421 VVLCNLKPQK MRGVESQGML LCASIEGINR QVEPLDPPAG SAPGEHVFVK GYEKGQPDEE
481 LKPKKKVFEK LQADFKISEE CIAQWKQTNF MTKLGSISCK SLKGGNIS
```

Figure 2.

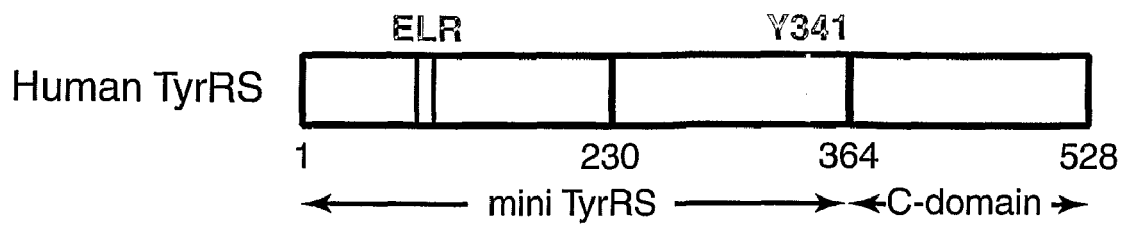
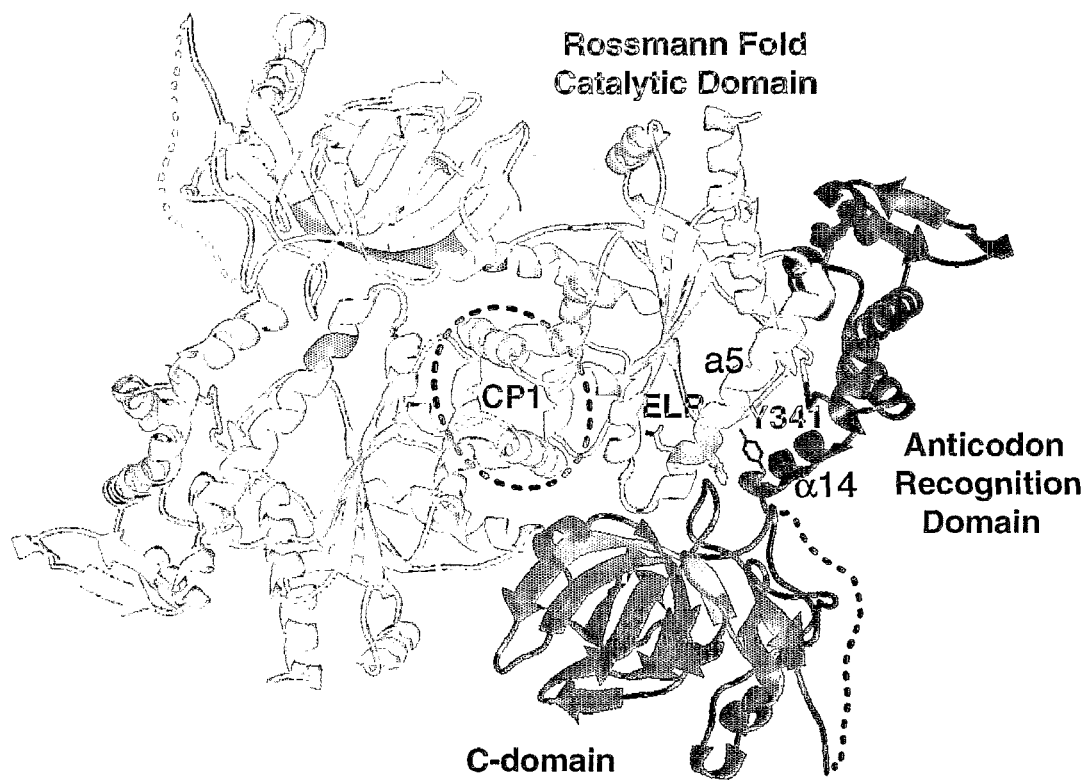
Figure 3.

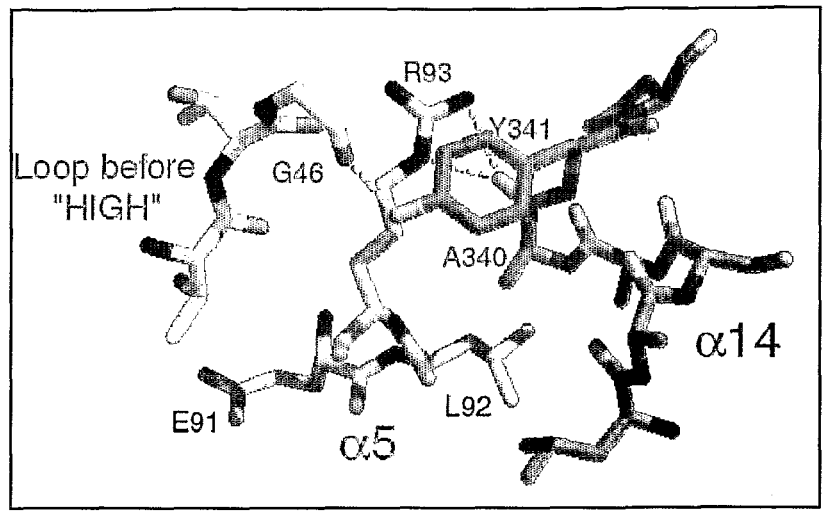

|       |        | REGION 1 |    | REGION 2 |    | REGION 3 |     |
|-------|--------|----------|----|----------|----|----------|-----|
|       |        | 39       | 55 | 87       | 97 | 337      | 346 |
| ROW 1 | H.sap  | YWGTATTG-KPHVAYFVP | | ....WELLELRVSYY | | ....ASAAYPDPSK | |
| ROW 2 | M.mus  | YWGTATTG-KPHVAYFVP | | ....WELLELRTSYY | | ....ASAAYPDPSK | |
| ROW 3 | B.tau  | YWGTATTG-KPHVAYFVP | | ....WDVLELRTSYY | | ....SSAAYPDPSK | |
| ROW 4 | D.mel  | YWGTATTG-KPHVAYFVP | | ....WSLLELRTKYY | | ....SAAAYPPPAK | |
| ROW 5 | C.ele  | YWGTATTG-KPHVGYLVP | | ....WELLKCRVIYY | | ....KEKGYNHSTD | |
| ROW 6 | S.cer  | YWGTAPTG-RPHCGYFVP | | ....LEVVNYRAKYY | | ....SEKGYPVATP | |
| ROW 7 | S.pom  | YWGSAPTG-RPHCGYFVP | | ....MELVQHRVRYY | | ....LKAAYPDPKD | |
| ROW 8 | E.col  | YCGFDPTADSLHLGHLVP | | ....LNTEETVQEWV | | ....DG-VPMVEME | |
| ROW 9 | B.sub  | YSGFDPTADSLHIGHLLP | | ....LNTADIVSEWS | | ....DVPSMEVDST | |

Figure 4.

Native Human TyrRS with enclosed ELR
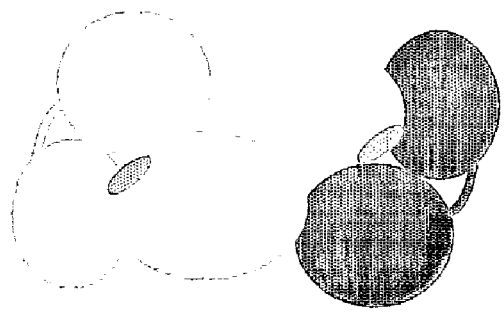
Y341A mutation or other sequence variants
Opened Human TyrRS with exposed ELR
Figure 6.

SEQUENCE LISTING

```
<160> NUMBER OF SEQ ID NOS: 26

<210> SEQ ID NO 1
<211> LENGTH: 4
<212> TYPE: PRT
<213> ORGANISM: Homo sapiens

<400> SEQUENCE: 1

His Ile Gly His
 1

<210> SEQ ID NO 2
<211> LENGTH: 5
<212> TYPE: PRT
<213> ORGANISM: Homo sapiens

<400> SEQUENCE: 2

Lys Met Ser Lys Ser
 1               5
```

```
<210> SEQ ID NO 3
<211> LENGTH: 528
<212> TYPE: PRT
<213> ORGANISM: Homo sapiens

<400> SEQUENCE: 3

Met Gly Asp Ala Pro Ser Pro Glu Glu Lys Leu His Leu Ile Thr Arg
  1               5                  10                  15

Asn Leu Gln Glu Val Leu Gly Glu Glu Lys Leu Lys Glu Ile Leu Lys
             20                  25                  30

Glu Arg Glu Leu Lys Ile Tyr Trp Gly Thr Ala Thr Thr Gly Lys Pro
         35                  40                  45

His Val Ala Tyr Phe Val Pro Met Ser Lys Ile Ala Asp Phe Leu Lys
 50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
             85                  90                  95

Tyr Glu Asn Val Ile Lys Ala Met Leu Glu Ser Ile Gly Val Pro Leu
        100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Pro Ala Lys Asn Ser Glu Pro Glu Val Ile Pro Ser Arg Leu
        355                 360                 365

Asp Ile Arg Val Gly Lys Ile Ile Thr Val Glu Lys His Pro Asp Ala
    370                 375                 380
```

```
Asp Ser Leu Tyr Val Glu Lys Ile Asp Val Gly Glu Ala Glu Pro Arg
385                 390                 395                 400

Thr Val Val Ser Gly Leu Val Gln Phe Val Pro Lys Glu Glu Leu Gln
                405                 410                 415

Asp Arg Leu Val Val Leu Cys Asn Leu Lys Pro Gly Lys Met Arg
            420                 425                 430

Gly Val Glu Ser Gln Gly Met Leu Leu Cys Ala Ser Ile Glu Gly Ile
            435                 440                 445

Asn Arg Gln Val Glu Pro Leu Asp Pro Pro Ala Gly Ser Ala Pro Gly
            450                 455                 460

Glu His Val Phe Val Lys Gly Tyr Glu Lys Gly Gln Pro Asp Glu Glu
465                 470                 475                 480

Leu Lys Pro Lys Lys Lys Val Phe Glu Lys Leu Gln Ala Asp Phe Lys
                485                 490                 495

Ile Ser Glu Glu Cys Ile Ala Gln Trp Lys Gln Thr Asn Phe Met Thr
            500                 505                 510

Lys Leu Gly Ser Ile Ser Cys Lys Ser Leu Lys Gly Gly Asn Ile Ser
            515                 520                 525
```

<210> SEQ ID NO 4
<211> LENGTH: 528
<212> TYPE: PRT
<213> ORGANISM: Artificial Sequence
<220> FEATURE:
<223> OTHER INFORMATION: Variant of human TyrRS
<221> NAME/KEY: VARIANT
<222> LOCATION: 341
<223> OTHER INFORMATION: Xaa = Gly, Ala, Phe, Val, Leu, Ile, Met, or
      Pro

<400> SEQUENCE: 4

```
Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
                20                  25                  30

Glu Arg Glu Leu Lys Ile Tyr Trp Gly Thr Ala Thr Thr Gly Lys Pro
            35                  40                  45

His Val Ala Tyr Phe Val Pro Met Ser Lys Ile Ala Asp Phe Leu Lys
        50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205
```

-continued

```
His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
                260                 265                 270

Ser Glu Phe Val Ile Leu Arg Asp Glu Lys Trp Gly Gly Asn Lys Thr
            275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Xaa Pro Asp Pro Ser Lys Gln Lys Pro Met Ala Lys
                340                 345                 350

Gly Pro Ala Lys Asn Ser Glu Pro Glu Glu Val Ile Pro Ser Arg Leu
            355                 360                 365

Asp Ile Arg Val Gly Lys Ile Ile Thr Val Glu Lys His Pro Asp Ala
    370                 375                 380

Asp Ser Leu Tyr Val Glu Lys Ile Asp Val Gly Glu Ala Glu Pro Arg
385                 390                 395                 400

Thr Val Val Ser Gly Leu Val Gln Phe Val Pro Lys Glu Glu Leu Gln
                405                 410                 415

Asp Arg Leu Val Val Leu Cys Asn Leu Lys Pro Gln Lys Met Arg
                420                 425                 430

Gly Val Glu Ser Gln Gly Met Leu Leu Cys Ala Ser Ile Glu Gly Ile
            435                 440                 445

Asn Arg Gln Val Glu Pro Leu Asp Pro Pro Ala Gly Ser Ala Pro Gly
    450                 455                 460

Glu His Val Phe Val Lys Gly Tyr Glu Lys Gly Gln Pro Asp Glu Glu
465                 470                 475                 480

Leu Lys Pro Lys Lys Lys Val Phe Glu Lys Leu Gln Ala Asp Phe Lys
                485                 490                 495

Ile Ser Glu Glu Cys Ile Ala Gln Trp Lys Gln Thr Asn Phe Met Thr
            500                 505                 510

Lys Leu Gly Ser Ile Ser Cys Lys Ser Leu Lys Gly Gly Asn Ile Ser
    515                 520                 525

<210> SEQ ID NO 5
<211> LENGTH: 17
<212> TYPE: PRT
<213> ORGANISM: Homo sapiens

<400> SEQUENCE: 5

Tyr Trp Gly Thr Ala Thr Thr Gly Lys Pro His Val Ala Tyr Phe Val
1               5                   10                  15

Pro

<210> SEQ ID NO 6
<211> LENGTH: 11
<212> TYPE: PRT
<213> ORGANISM: Homo sapiens

<400> SEQUENCE: 6
```

```
Trp Glu Leu Leu Glu Leu Arg Val Ser Tyr Tyr
 1               5                   10

<210> SEQ ID NO 7
<211> LENGTH: 10
<212> TYPE: PRT
<213> ORGANISM: Homo sapiens

<400> SEQUENCE: 7

Ala Ser Ala Ala Tyr Pro Asp Pro Ser Lys
 1               5                   10

<210> SEQ ID NO 8
<211> LENGTH: 11
<212> TYPE: PRT
<213> ORGANISM: Bos taurus

<400> SEQUENCE: 8

Trp Asp Val Leu Glu Leu Arg Thr Ser Tyr Tyr
 1               5                   10

<210> SEQ ID NO 9
<211> LENGTH: 10
<212> TYPE: PRT
<213> ORGANISM: Bos taurus

<400> SEQUENCE: 9

Ser Ser Ala Ala Tyr Pro Asp Pro Ser Lys
 1               5                   10

<210> SEQ ID NO 10
<211> LENGTH: 11
<212> TYPE: PRT
<213> ORGANISM: Drosophila melanogaster

<400> SEQUENCE: 10

Trp Ser Leu Leu Glu Leu Arg Thr Lys Tyr Tyr
 1               5                   10

<210> SEQ ID NO 11
<211> LENGTH: 10
<212> TYPE: PRT
<213> ORGANISM: Drosophila melanogaster

<400> SEQUENCE: 11

Ser Ala Ala Ala Tyr Pro Pro Pro Ala Lys
 1               5                   10

<210> SEQ ID NO 12
<211> LENGTH: 17
<212> TYPE: PRT
<213> ORGANISM: Caenorhabditis elegans

<400> SEQUENCE: 12

Tyr Trp Gly Thr Ala Thr Thr Gly Lys Pro His Val Gly Tyr Leu Val
 1               5                   10                  15

Pro

<210> SEQ ID NO 13
<211> LENGTH: 11
<212> TYPE: PRT
<213> ORGANISM: Caenorhabditis elegans

<400> SEQUENCE: 13
```

```
Trp Glu Leu Leu Lys Cys Arg Val Ile Tyr Tyr
 1               5                  10
```

<210> SEQ ID NO 14
<211> LENGTH: 10
<212> TYPE: PRT
<213> ORGANISM: Caenorhabditis elegans

<400> SEQUENCE: 14

```
Lys Glu Lys Gly Tyr Asn His Ser Thr Asp
 1               5                  10
```

<210> SEQ ID NO 15
<211> LENGTH: 17
<212> TYPE: PRT
<213> ORGANISM: Saccharomyces cerevisiae

<400> SEQUENCE: 15

```
Tyr Trp Gly Thr Ala Pro Thr Gly Arg Pro His Cys Gly Tyr Phe Val
 1               5                  10                  15

Pro
```

<210> SEQ ID NO 16
<211> LENGTH: 11
<212> TYPE: PRT
<213> ORGANISM: Saccharomyces cerevisiae

<400> SEQUENCE: 16

```
Leu Glu Val Val Asn Tyr Arg Ala Lys Tyr Tyr
 1               5                  10
```

<210> SEQ ID NO 17
<211> LENGTH: 10
<212> TYPE: PRT
<213> ORGANISM: Saccharomyces cerevisiae

<400> SEQUENCE: 17

```
Ser Glu Lys Gly Tyr Pro Val Ala Thr Pro
 1               5                  10
```

<210> SEQ ID NO 18
<211> LENGTH: 17
<212> TYPE: PRT
<213> ORGANISM: Saccharomyces pombe

<400> SEQUENCE: 18

```
Tyr Trp Gly Ser Ala Pro Thr Gly Arg Pro His Cys Gly Tyr Phe Val
 1               5                  10                  15

Pro
```

<210> SEQ ID NO 19
<211> LENGTH: 11
<212> TYPE: PRT
<213> ORGANISM: Saccharomyces pombe

<400> SEQUENCE: 19

```
Met Glu Leu Val Gln His Arg Val Arg Tyr Tyr
 1               5                  10
```

<210> SEQ ID NO 20
<211> LENGTH: 10
<212> TYPE: PRT
<213> ORGANISM: Saccharomyces pombe

<400> SEQUENCE: 20

```
Leu Lys Ala Ala Tyr Pro Asp Pro Lys Asp
 1               5                  10
```

<210> SEQ ID NO 21
<211> LENGTH: 18
<212> TYPE: PRT
<213> ORGANISM: Escherichia coli

<400> SEQUENCE: 21

```
Tyr Cys Gly Phe Asp Pro Thr Ala Asp Ser Leu His Leu Gly His Leu
 1               5                  10                  15

Val Pro
```

<210> SEQ ID NO 22
<211> LENGTH: 11
<212> TYPE: PRT
<213> ORGANISM: Escherichia coli

<400> SEQUENCE: 22

```
Leu Asn Thr Glu Glu Thr Val Gln Glu Trp Val
 1               5                  10
```

<210> SEQ ID NO 23
<211> LENGTH: 9
<212> TYPE: PRT
<213> ORGANISM: Escherichia coli

<400> SEQUENCE: 23

```
Asp Gly Val Pro Met Val Glu Met Glu
 1               5
```

<210> SEQ ID NO 24
<211> LENGTH: 18
<212> TYPE: PRT
<213> ORGANISM: Bacillus subtilis

<400> SEQUENCE: 24

```
Tyr Ser Gly Phe Asp Pro Thr Ala Asp Ser Leu His Ile Gly His Leu
 1               5                  10                  15

Leu Pro
```

<210> SEQ ID NO 25
<211> LENGTH: 11
<212> TYPE: PRT
<213> ORGANISM: Bacillus subtilis

<400> SEQUENCE: 25

```
Leu Asn Thr Ala Asp Ile Val Ser Glu Trp Ser
 1               5                  10
```

<210> SEQ ID NO 26
<211> LENGTH: 10
<212> TYPE: PRT
<213> ORGANISM: Bacillus subtilis

<400> SEQUENCE: 26

```
Asp Val Pro Ser Met Glu Val Asp Ser Thr
 1               5                  10
```

ANGIOGENIC TYROSYL TRNA SYNTHETASE COMPOSITIONS AND METHODS

CROSS-REFERENCE TO RELATED APPLICATIONS

This application claims the benefit of U.S. Provisional Application for Patent Ser. No. 60/741,580, filed on Dec. 2, 2005, which is incorporated herein by reference.

STATEMENT OF GOVERNMENT INTEREST

A portion of the work described herein was supported by grant number CA 92577 from the National Institutes of Health. The United States Government has certain rights in this invention.

FIELD OF THE INVENTION

This invention relates to angiogenic tyrosyl-tRNA synthetase (TyrRS) compositions. More particularly this invention relates to angiogenic TyrRS protein variants and angiogenic fragments thereof, and to methods of stimulating angiogenesis therewith.

BACKGROUND OF THE INVENTION

Aminoacyl-tRNA synthetases are essential enzymes that catalyze the addition of amino acids to their cognate tRNAs as a first step in protein synthesis. These essential enzymes are separated into two classes based on the presence of unique sequence motifs and overall structure of their catalytic domains. Class I synthetases have two highly conserved amino acid motifs, i.e., the sequences HIGH (SEQ ID NO: 1) and KMSKS (SEQ ID NO: 2), within the catalytic domains of its ten members. In contrast, the Class II synthetases have three highly degenerate sequence motifs, referred to as motifs 1-3. Over the past twenty years, several additional roles for tRNA synthetases were discovered, including RNA splicing, nuclear export and regulation of gene transcription. These additional functions have been acquired during the long evolution of these ancient enzymes. Many of these added functions are a result of appended domains, which have been fused to the core synthetase sequences. In higher eucaryotes, the appended domains of two synthetases have been demonstrated to have functional biological roles unrelated to the function of the core enzyme. For instance, fragments of two human tRNA synthetases, i.e., tyrosyl-tRNA synthetase (TyrRS) and tryptophanyl-tRNA synthetase (TrpRS), have been demonstrated to have cytokine-like activities. Two related fragments of human TrpRS, known as mini-TrpRS and T2-TrpRS, are negative regulators of angiogenesis. Human TyrRS (SEQ ID NO: 3) can be readily separated into two active fragments. A C-terminal appended domain fragment has activity similar to the pro-inflammatory cytokine endothelial-monocyte-activating polypeptide II (EMAP II), while an N-terminal fragment (mini-TyrRS, residues 1-364 of SEQ ID NO: 3) induces angiogenesis.

Angiogenesis is a tightly regulated process in which a careful balance between pro-angiogenic and anti-angiogenic factors must be maintained. Disruption of this balance, leading to excessive or insufficient growth of blood vessels, is associated with diseases such as age-related macular degeneration, rheumatoid arthritis, delayed wound healing, as well as many other conditions. Regulation is controlled through a variety of processes including transcriptional and translational control, post-translational modifications and processing of the ligand. Other proangiogenic cytokines, including tumor necrosis factor-alpha and hepatocyte growth factor, are generated by proteolytic cleavage of precursor proteins. Similarly, cleavage by proteases releases active cytokine fragments from human TrpRS and TyrRS.

The TrpRS and TyrRS enzymes of higher eukaryotes are composed of a core catalytic region that includes a Rossmann fold having a number of alpha coils interspersed with beta sheet segments. The Rossmann fold catalytic domain of human TyrRS (residues 1 through 230 of SEQ ID NO: 3) includes a hydrogen bond tether between the α5 coil of the Rossmann fold domain and the α14 coil of the anticodon recognition domain (see FIG. 3, Bottom Panel, and FIG. 4, Top Panel). The tether partially blocks the Glu-Leu-Arg (ELR) motif in the α5 coil of the active site domain of the protein.

The catalytic domain of human TyrRS and TrpRS are each homologous to the catalytic domains of their respective corresponding bacterial and lower eukaryotic enzymes, appended with a C-terminal or N-terminal extension, respectively. The C-terminal extension of human TyrRS shares about 51% sequence identity to the pro-inflammatory cytokine EMAP II. In each case, the full-length enzymes are inactive as cytokines, though functional as synthetases. When the extensions unique to higher eukaryotes are removed, the enzymes become active cytokines capable of controlling angiogenesis.

It has now been discovered that opening the separation between the α5 coil of the catalytic Rossmann fold domain and the α14 coil of the anticodon recognition domain relative to the separation of these coils in native human TyrRS renders the protein angiogenic. The present invention provides TyrRS protein variants and fragments thereof, which are useful for stimulating angiogenesis in mammalian tissues.

SUMMARY OF THE INVENTION

The present invention provides a biologically active TyrRS polypeptide variant, and angiogenic fragments thereof (collectively referred to herein as "TyrRS polypeptide variants"), which are suitable for stimulating angiogenesis in mammalian tissues. The isolated tyrosyl tRNA synthetase (TyrRS) polypeptide variants of the invention comprise a Rossmann fold domain or a portion thereof; an anticodon recognition domain or a portion thereof; and include at least one non-conservative amino acid residue substitution relative to the amino acid residue sequence of human TyrRS (SEQ ID NO: 3). The variants exhibit an angiogenic activity that is greater than the angiogenic activity of native human TyrRS. Preferably, the TyrRS polypeptide variants of the invention have an amino acid residue sequence identity of at least 50% compared to the amino acid residue sequence of human TyrRS (SEQ ID NO: 3), more preferably at least 80% sequence identity, most preferably at least about 95% sequence identity compared to SEQ ID NO: 3. Preferably, the TyrRS polypeptide variants include a non-conservative amino acid residue substitution of an amino acid residue at one or more of positions corresponding to positions 46, 340, and 341 of SEQ ID NO: 3.

In a preferred embodiment, the TyrRS polypeptide variant of the invention comprises a Rossmann fold region or a portion thereof, which includes an α5 coil, as well as an anticodon recognition domain or a portion thereof that includes an α14 coil. The TyrRS polypeptide variant has an amino acid residue sequence that has a sequence identity of at least about 50% compared to the amino acid residue sequence of native human TyrRS (SEQ ID NO: 3, FIG. 1). The variant includes at least one non-conservative amino acid residue substitution relative to the amino acid residue sequence of human TyrRS, which opens up the separation between the α5 coil and the α14 coil, relative to the separation of the α5 coil and the α14 coil in native human TyrRS. Preferably, the α14 coil is separated by at least about 6 Angstroms from the α5 coil in the tertiary structure of the variant, as determined by the spatial separation between the alpha-carbon of any amino acid residue of the α14 coil and the alpha-carbon of any amino acid residue of the α5 coil. The variant preferably is free from hydrogen bonds between the α5 coil and the α14 coil.

In another preferred embodiment of the TyrRS polypeptide variant of the invention the α5 coil includes an ELR motif, and the α14 coil is spaced at least about 6 Angstroms from the ELR motif of the α5 coil in the tertiary structure of the variant, as determined by the spatial separation between the alpha-carbon of any amino acid residue of the α14 coil and the alpha-carbon of any amino acid residue of the ELR motif of the α5 coil. The variant presents an exposed ELR motif on an external portion of the polypeptide tertiary structure. The TyrRS polypeptide variant has an amino acid residue sequence identity of at least about 50% compared to the amino acid residue sequence of human TyrRS (SEQ ID NO: 3, FIG. 1), and includes at least one non-conservative amino acid residue substitution relative to the amino acid residue sequence of human TyrRS, which precludes formation of a hydrogen bond tether between the ELR motif of the α5 coil and the amino acid residues of the α14 coil of the TyrRS polypeptide variant, or which otherwise results in exposure of the ELR motif in the tertiary structure of the variant.

In yet another preferred embodiment, the TyrRS polypeptide variant includes a non-conservative amino acid residue substitution at an amino acid residue corresponding to one or more of positions 46, 340, and 341 of SEQ ID NO: 3. A particularly preferred substitution is replacement of the amino acid corresponding to the tyrosine at position 341 of SEQ ID NO: 3 with an amino acid residue having an aliphatic side chain, preferably a non-polar aliphatic side chain, such as an alanine residue.

The TyrRS variants of the invention are suitable for stimulating angiogenesis in mammalian (e.g., human) tissues.

The present invention also provides methods of stimulating angiogenesis and endothelial cell migration in a tissue of a mammal by contacting the tissue with a TyrRS polypeptide variant of the invention, as described herein.

BRIEF DESCRIPTION OF THE DRAWINGS

FIG. 1 shows the amino acid residue sequence of human TyrRS (SEQ ID NO: 3).

FIG. 2 shows the amino acid residue sequence of a preferred human TyrRS variant of the invention (SEQ ID NO: 4).

FIG. 3 (Top Panel) shows a schematic diagram of the wild-type human TyrRS sequence, which is composed of 3 domains: the Rossmann fold catalytic domain (yellow, residues 1-230), the anticodon recognition domain (green, residues 231-364) and the C-terminal domain (purple, residues 364-528). The first two domains form the active core enzyme, which is called mini TyrRS (residues 1-364). The Bottom Panel shows a dimeric model of human TyrRS based on crystal structures of both mini TyrRS and the C-domain, which were experimentally determined.

FIG. 4 (Top Panel) shows details of the interaction of the ELR region with other residues, including Y341. The Bottom Panel shows a partial sequence alignment of TyrRS from a range of organisms in which residues corresponding to three regions of human TyrRS are aligned, i.e., residues 39-55 (Region 1), residues 87-97 (Region 2), and residues 337-346 (Region 3). Conserved residues involved in the domain contacts are highlighted. Row 1 includes amino acid residues of human TyrRS, in which Region 1 corresponds to SEQ ID NO: 5, Region 2 corresponds to SEQ ID NO: 6, and Region 3 corresponds to SEQ ID NO: 7. Row 2 shows alignment of murine TyrRS, in which Region 1 corresponds to SEQ ID NO: 5, Region 2 corresponds to SEQ ID NO: 6, and Region 3 corresponds to SEQ ID NO: 7, as in human TyrRS. Row 3 shows alignment of bovine TyrRS in which Region 1 corresponds to SEQ ID NO: 5, Region 2 corresponds to SEQ ID NO: 8, and Region 3 corresponds to SEQ ID NO: 9. Row 4 shows alignment of *Drosophila melanogaster* TyrRS in which Region 1 corresponds to SEQ ID NO: 5, Region 2 corresponds to SEQ ID NO: 10, and Region 3 corresponds to SEQ ID NO: 11. Row 5 shows alignment of *Caenorhabditis elegans* TyrRS in which Region 1 corresponds to SEQ ID NO: 12, Region 2 corresponds to SEQ ID NO: 13, and Region 3 corresponds to SEQ ID NO: 14. Row 6 shows alignment of *Saccharomyces cerevisiae* TyrRS in which Region 1 corresponds to SEQ ID NO: 15, Region 2 corresponds to SEQ ID NO: 16, and Region 3 corresponds to SEQ ID NO: 17. Row 7 shows alignment of *Saccharomyces pombe* TyrRS in which Region 1 corresponds to SEQ ID NO: 18, Region 2 corresponds to SEQ ID NO: 19, and Region 3 corresponds to SEQ ID NO: 20. Row 8 shows alignment of *Escherichia coli* TyrRS in which Region 1 corresponds to SEQ ID NO: 21, Region 2 corresponds to SEQ ID NO: 22, and Region 3 corresponds to SEQ ID NO: 23. Row 9 shows alignment of *Bacillus subtilis* TyrRS in which Region 1 corresponds to SEQ ID NO: 24, Region 2 corresponds to SEQ ID NO: 25, and Region 3 corresponds to SEQ ID NO: 26.

FIG. 6 schematically illustrates the opening effect of the Y341A mutation on the overall tertiary structure of human TyrRS, which exposes the ELR motif. The Y341A mutation was demonstrated by SAXS analysis and protease digestion studies to open up the TyrRS structure, as shown.

DETAILED DESCRIPTION OF PREFERRED EMBODIMENTS

Figure 5:
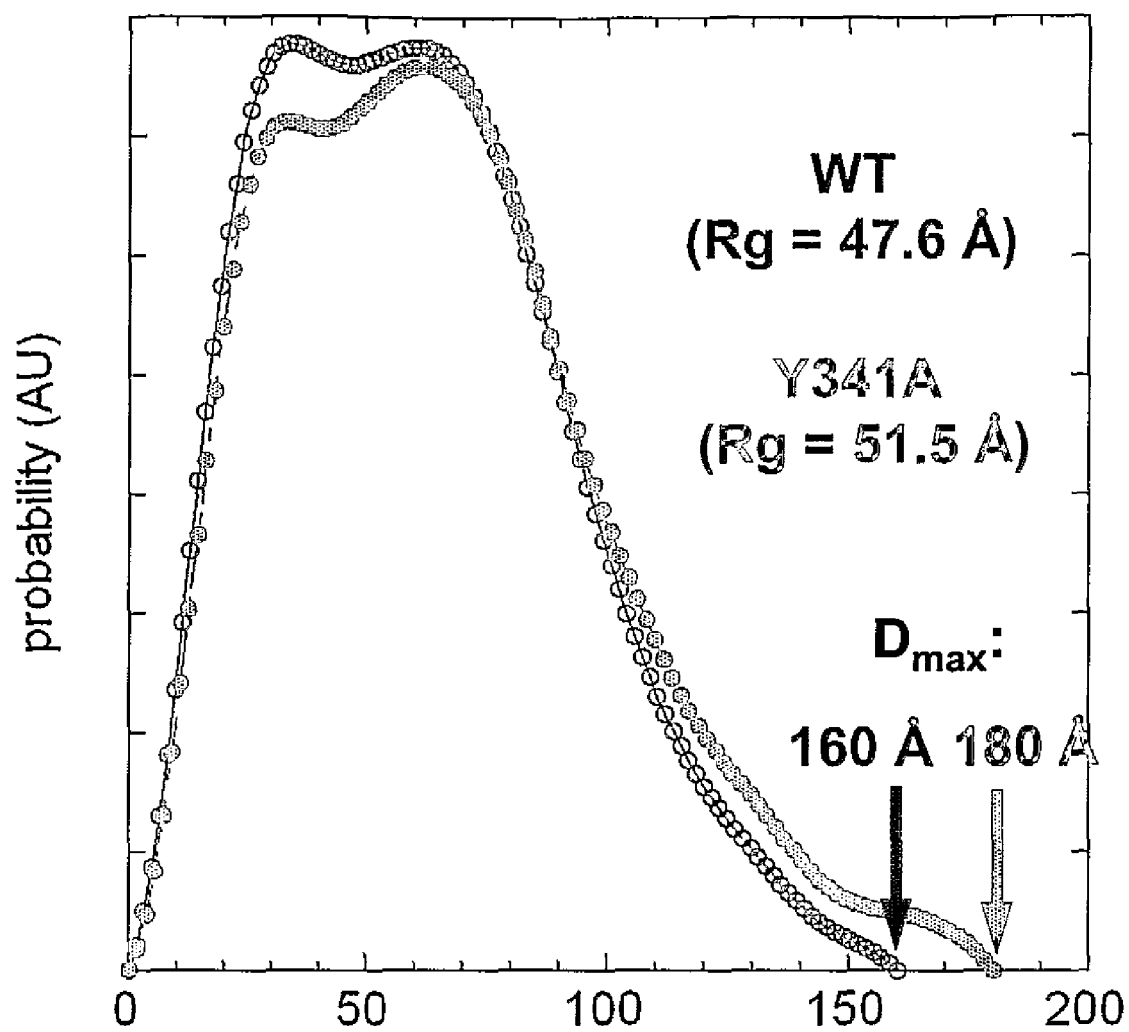
FIG. 5 shows an X-ray scattering distribution for human TyrRS and TyrRS-Y341A. The electron pair distance distribution functions were calculated for human TyrRS and the Y341A mutation of TyrRS using their measured small angel x-ray scattering (SAXS) curves. Radius of Gyration ($R_g$) and Maximum distance ($D_{max}$) were calculated for both molecules. Y341A has an $R_g$ that is about 4 Angstroms larger, and a $D_{max}$ that is about 20 angstroms larger, than those of wild-type TyrRS.

Amino acid residues in proteins have been classified in a variety of ways, primarily based on the physico-chemical characteristics imparted by the side chains of the amino acids. For example, one common classification includes three categories of amino acids: (1) hydrophobic (non-polar) amino acids, including glycine, alanine, valine, phenylalanine, proline, methionine, isoleucine, and leucine; (2) charged amino acids, including aspartic acid, glutamic acid, lysine, and arginine; and (3) polar amino acids, including serine, threonine, tyrosine, histidine, cysteine, asparagine, glutamine, and tryptophan; glycine is sometimes included as its own, forth category (see Chapter 1 of Branden and Tooze, *Introduction to Protein Structure*, Second Edition, Garland Publishing, Inc. 1998, pages 3-12, which is incorporated herein by reference).

Amino acid residues can also be further categorized based on whether their side chains are aliphatic or aromatic, small or bulky, polar or non-polar, charged or non-charged, combinations thereof, and the like. As used herein, non-polar, aliphatic amino acids include glycine, alanine, valine, leucine, isoleucine, methionine, and proline; non-charged, bulky amino acids include tyrosine, tryptophan, phenylalanine, leucine, isoleucine, and methionine; small, non-polar amino acids include glycine, alanine, and proline.

As used herein and in the appended claims, the term "non-conservative", when used in relation to amino acid residue substitutions means the substitution of an amino acid residue in a wild-type or natural protein with an amino acid residue of a significantly different structural category, e.g., having a significantly different polarity classification (i.e., non-polar versus polar), size classification, charge classification, a combination thereof, and the like. For example, for a non-conservative substitution, a polar amino acid such as tyrosine can be replaced by a non-polar amino acid, a relatively small non-polar amino acid, and the like; while a small non-polar amino acid such as glycine or alanine can be replaced by a bulky amino acid, a charged amino acid, and the like.

An preferred isolated TyrRS polypeptide variant embodying the present invention is suitable for stimulating angiogenesis in mammalian tissues and comprises a Rossmann fold region or a portion thereof, which includes an α5 coil, as well as an anticodon recognition domain or a portion thereof that includes an α14 coil. The variant has a separation between the α5 coil and the α14 coil in the variant, which is greater than the separation between the α5 coil and the α14 coil in native human TyrRS. Preferably, the α14 coil is separated from the α5 coil by at least about 6 Angstroms in the tertiary structure of the variant, as determined by the spatial separation between the alpha-carbon of any amino acid residue of the α14 coil and the alpha-carbon of any amino acid residue of the α5 coil. The variant preferably is free from hydrogen bonds between the α5 coil and the α14 coil. The TyrRS polypeptide variant has an amino acid residue sequence identity of at least about 50% compared to the amino acid residue sequence of native human TyrRS (SEQ ID NO: 3, FIG. 1), more preferably at least about 80%, most preferably at least about 95% sequence identity. The variant includes at least one non-conservative amino acid residue substitution relative to the amino acid residue sequence of human TyrRS, which opens up the separation between the α5 coil and the α14 coil, relative to the separation of the α5 coil and the α14 coil in native human TyrRS, and confers angiogenic activity to the variant.

In another preferred embodiment, the TyrRS variant of the invention comprises a Rossmann fold region or a portion thereof that presents an exposed ELR motif on an external portion of the tertiary structure of the polypeptide, and which has an amino acid residue sequence identity of at least about 50% compared to the amino acid residue sequence of human TyrRS (SEQ ID NO: 3), preferably at least about 80%, more preferably about 95% sequence identity. The TyrRS polypeptide variant includes at least one non-conservative amino acid residue substitution relative to the amino acid residue sequence of human TyrRS, which exposes the ELR motif of the α5 coil of the catalytic Rossmann fold domain, thereby rendering the polypeptide angiogenic. In the variants of the invention, the ELR residues of the α5 coil preferably are spaced at least about 6 Angstroms from and the residues of the α14 coil each in the tertiary structure of the variant, as determined by the spatial separation between the alpha-carbon of any amino acid residue of the α14 coil and the alpha-carbon of any amino acid residue of the ELR motif of the α5 coil.

Preferably, the at least one non-conservative amino acid residue substitution is a substitution of an amino acid residue at one or more of positions corresponding to amino acid residues 46, 340, and 341 of SEQ ID NO: 3. For example, the tyrosine at position 341 of SEQ ID NO: 3 preferably is replaced by an amino acid residue having a non-polar side chain (e.g., a non-polar, aliphatic amino acid, such as glycine, alanine, valine, leucine, isoleucine, methionine, and proline). The amino acid residue corresponding to the glycine at position 46 and/or the alanine at position 340 of SEQ ID NO: 3 preferably is replaced by an amino acid residue having a bulky non-polar side chain (e.g., a large non-charged, hydrophobic amino acid such as tyrosine, tryptophan, phenylalanine, leucine, isoleucine, or methionine). As used herein, a reference to an amino acid in a TyrRS polypeptide variant "corresponding to" an amino acid residue within a specified sequence, such as SEQ ID NO: 3, means an amino acid at a position in the homologous sequence of the TyrRS polypeptide variant, which aligns with (i.e., corresponds to) the specified position in SEQ ID NO: 3 when the homologous sequence is compared to the specified sequence. One of ordinary skill in the protein arts will understand that the numbering of the amino acid residue in the homologous sequence may be different from the numbering in the specified sequence (e.g., SEQ ID NO: 3).

In yet another embodiment, an isolated TyrRS polypeptide variant of the present invention comprises a Rossmann fold region or a portion thereof that presents an exposed ELR motif on an external portion of the protein or fragment and has an amino acid residue sequence identity of at least about 50% compared to the amino acid residue sequence of human TyrRS (SEQ ID NO: 3). Preferably, the amino acid residue sequence of the variant has a sequence identity of at least about 80% compared to SEQ ID NO: 3, more preferably about 95%, and includes an amino acid residue having a non-polar side chain at the position corresponding to position 341 of SEQ ID NO: 3. Preferably, the amino acid residue has a non-polar, aliphatic side chain. For example, the amino acid residue of the variant corresponding to tyrosine residue 341 of human TyrRS can be a glycine residue, an alanine residue, a phenylalanine residue, a valine residue, a leucine residue, an isoleucine residue, a methionine residue, or a proline residue. In some embodiments, the amino acid residue corresponding to tyrosine 341 of human TyrRS is a glycine residue, an alanine residue, or a proline residue, preferably an alanine residue.

In another preferred embodiment, the isolated TyrRS polypeptide variant comprises the amino acid residue sequence of SEQ ID NO: 4 (FIG. 2) or a fragment thereof, wherein residue X at position 341 of SEQ ID NO: 4 is a glycine residue, an alanine residue, a phenylalanine residue, a valine residue, a leucine residue, an isoleucine residue, a methionine residue, or a proline residue, preferably a glycine, alanine, or proline residue, more preferably an alanine residue. Preferably, the TyrRS polypeptide variant comprises the entire N-terminal region (i.e., residues 1-364) of SEQ ID NO: 4. Preferably, a fragment includes at least residues of the α5 chain of the Rossmann fold region, i.e., residues corresponding to positions 87 through 104 of SEQ ID NO: 4. More preferably, the fragment encompasses the entire Rossmann fold region (residues 1-230 of SEQ ID NO: 4).

A particularly preferred angiogenic TyrRS polypeptide variant of the invention consists of the amino acid residue sequence of SEQ ID NO: 4, wherein residue X at position 341 of SEQ ID NO: 4 is selected from the group consisting of a glycine residue, an alanine residue, a phenylalanine residue, a valine residue, a leucine residue, an isoleucine residue, a methionine residue, and a proline residue. More preferably, residue X at position 341 of SEQ ID NO: 4 is selected from the group consisting of a glycine residue, an alanine residue, and a proline residue, most preferably an alanine residue.

The present invention also provides a method of stimulating angiogenesis in the tissue of a mammal. The method comprises contacting the tissue with an angiogenic amount of a TyrRS polypeptide variant of the invention as described in detail herein.

In another aspect, the present invention provides a method of stimulating endothelial cell migration in the tissue of a mammal. The method comprises contacting the tissue with an endothelial cells migration stimulating amount of a TyrRS polypeptide variant of the invention as described in detail herein.

Methods and Procedures.

Plasmid Construction. TyrRS-Y341A and mini-TyrRS-Y341A plasmids were constructed using the QuikChange site-directed mutagenesis kit (Stratagene, La Jolla, Calif.). Templates were pET20b(+) (Novagen, Masdison, Wis.) vectors containing the wild-type TyrRS and mini-TyrRS, respectively. All proteins were expressed with a C-terminal His-Tag to facilitate isolation of the polypeptide. Synthetic oligonucleotides were purchased from Invitrogen Corporation (Carlsbad, Calif.).

Protein Production and Endotoxin Removal. Recombinant polypeptides were expressed in *E. coli* B121-CodonPlus (DE3)-RIL cells (Stratagene, La Jolla, Calif.). Cells were grown to an $OD_{600}$ of 0.8, and induced for 3 hours with 1 mM isopropyl β-D-thiogalactopyranoside (Roche, Basel, Switzerland). Cells were then pelleted and resuspended in Buffer A (20 mM Tris-HCl, pH 7.9, 30 mM imidazole, 500 mM NaCl). Following lysis by sonication, cell debris was separated by centrifugation at 74,000 g for 30 minutes. The His-tagged polypeptides were purified by Ni-NTA affinity chromatography. Supernatant was loaded onto a Ni-NTA affinity column (Qiagen, Valencia, Calif.), washed with 100 mL Buffer B (Buffer A with 0.1% Triton-X114 (Sigma, St. Louis, Mo.)) and 150 mL Buffer A. Polypeptides were eluted by a linear gradient of Buffer A and Buffer C (20 mM Tris-HCl, pH 7.9, 250 mM imidazole, 500 mM NaCl). Fractions containing >95% pure polypeptides were pooled, concentrated and dialyzed into storage buffer (50% phosphate buffered saline, PBS, pH 7.4, 50% glycerol, 2 mM dithiothreitol, DTT). Protein concentration was determined by Bradford assay using the Bio-Rad Protein Assay reagent (Bio-Rad, Hercules, Calif.) with bovine serum albumin (BSA, Sigma, St. Louis, Mo.) as a standard. Endotoxin concentration was determined using the Limulus Amebocyte Lysate (LAL) assay (BioWhittaker, Walkersville, Md.).

Small angel X-ray scattering. Small Angel X-ray scattering (SAXS) measurements were conducted for the wild-type TyrRS and the TyrRS-Y341A variant of the invention on beamline 4-2 at the Stanford Synchrotron Radiation Laboratory (SSRL). X-ray scattering curves were measured for samples at various concentrations (2-20 g/L). The x-ray wavelength (λ) was 1.38 Å and the detector channel numbers were converted to the momentum transfer $Q=4\pi*\sin\theta/\lambda$, where 2*θ is the scattering angle. Two different sample-to-detector distances were used to cover very small to medium scattering angles, i.e., 2.5 meters covering a Q range of about 0.01-0.25 Å$^{-1}$, and 0.5 meters to cover a Q range of about 0.03-0.93 Å$^{-1}$.

A polycarbonate cell with mica windows was filled with a sample aliquot and held at 20° C. throughout the measurement. A MarCCD 165 detector was used throughout the data collection. A typical set of data collection consisted of 24 two-dimensional scattering images recorded in series for 10 seconds each. A series of data were processed along with the matching buffer scattering data, typically recorded either immediately after or before the protein solution measurement. The data were scaled for the integrated beam intensity, azimuthally averaged, inspected for time-dependent changes, which are usually caused by radiation damage, and statistically analyzed. About 1.5 times higher statistical variations of the protein data over the variation of the matching buffer data were allowed in the averaging. Any data frame that showed a higher level of deviation with respect to the first protein scattering data frame beyond that level was rejected. The processed buffer scattering curves were subtracted from the corresponding protein scattering curves after the above data processing.

The scaling of small-angle and high-angle data were performed by the PRIMUS software program (Konarev et al. 2003. "PRIMUS: a Windows PC-based system for small-angle scattering data analysis", *J. Appl. Crystallogr.* 36:1277-1282), which was also used to compute $R_g$ and I(Q=0) by a Guinier plot in the $Q*R_g$ range of 0.45-1.3. The electron pair distance distribution function P(r) was obtained by the indirect Fourier transfer of the experimental data using the GNOM small-angle scattering data processing program of Svergun et al. (available from the embl-hamburg(dot)de website), initially with the small-angle data only to obtain accurate estimate of the maximum distance ($D_{max}$) P(r) was then recomputed including the high-angle data with the specified $D_{max}$ values above for model construction.

Protease digestion. Wild type TyrRS and TyrRS-Y341A were mixed with plasmin or leukocyte elastase at a protein-to-protease ratio of about 32 μg to 1 μg of plasmin, and 2500 μg per unit for the elastase. The mixtures were incubated at 20° C. for about 2 hours before the reactions were stopped by addition of formic acid to a final concentration of 0.1%. The cleavage fragments in the mixtures were analyzed by MALDI TOF mass spectrometry and by N-terminal sequencing using Edman degradation.

CAM Angiogenesis Assay. Chick chorioallantoic membrane (CAM) angiogenesis assays were performed by the following procedure. Fertilized complement fixation for avian leukosis virus (COFAL)-negative eggs (Charles River Labs, Storrs, Conn.) were incubated for 3.5 days at 38°

C./60% humidity. Eggs were then opened and the embryos were transferred into sterile plastic weigh boats. The embryos were covered and incubated at 37.5° C./90% humidity. After five days, collagen/mesh onplants containing about 30 µL of PBS, VEGF and bFGF (about 0.15 and 0.5 µg, respectively) or TyrRS polypeptides (1 µM) were placed onto the CAM membrane of the embryos, and incubated for an additional 66 hours. The upper mesh layers of the implants were examined under a stereomicroscope and scored for the proportion of "boxes" (i.e., three dimensional regions defined by the mesh fibers), which contain a blood vessel relative to the total number of boxes.

Murine Matrigel Angiogenesis Assay. Athymic wehi mice were subcutaneously implanted with 400 µL of growth-factor-depleted Matri gel (Becton Dickinson) supplemented with PBS, 20 nM VEGF or 250 nM TyrRS, mini-TyrRS, TyrRS-Y341A or mini-TyrRS-Y341A. Five days later, the mice were injected intravenously with fluorescein-labeled endothelial binding lectin Griffonia (Bandeiraea) Simplicifolia I, isolectin B4 (GSL-B4) (Vector Laboratories, Burlingame, Calif.). Matrigel plugs were resected and homogenized in radioimmuno-precipitation (RIPA) buffer (10 mM sodium phosphate, pH 7.4, 150 mM sodium chloride, 1% Nonidet P-40, 0.5% sodium deoxycholate, 0.1% sodium dodecyl sulfate). Following homogenization, the fluorescein content of each plug was quantified by spectrophotometric analysis.

Endothelial Cell Migration Assay. Human umbilical vein endothelial cells (HUVECs) (Cambrex) were plated at a density of about $3\times10^5$ cells/well of a 6-well plate in EGM media (Cambrex) containing 10% fetal bovine serum (FBS) and grown to confluent monolayers. Cells were starved in media containing no FBS for 16 hours and wounded across the well with a pipette tip. The wounded layers were washed twice with serum-free media to remove cell debris and the cells were allowed to migrate in the presence and absence of TyrRS variants and control factors. Images of the cell-free wound area were taken at 0 and 6 hours post wounding and analyzed using an image analysis software (NIH ImageJ 1.33). Endothelial cell migration was calculated as the percentage of the remaining cell-free area compared to the area of the initial wound, from which the % area closed for each condition was determined.

Amino Acid Activation. Amino acid activation was assayed by ATP-pyrophosphate (PPi) exchange reaction. Reactions were performed at 37° C. in buffer containing Tris-HCl (100 mM, pH 7.8), KF (10 mM), $MgCl_2$ (2 mM), ATP (1 mM), BSA (0.1 mg/mL), NaPPi (2 mM, 130 cpm/nmole), beta-mercaptoethanol (5 mM), tyrosine (2 mM) and 200 nM of the polypeptide.

Results and Discussion

Residue Y341 of TyrRS secured the structure around the ELR motif. It is known that mini-TyrRS (i.e., amino acid residues 1-364 of human TyrRS), but not full-length TyrRS, acts as a pro-angiogenic cytokine. Pro-angiogenic activity is dependent upon the presence of an ELR motif, which is also present in and required for activity of CXC chemokines, such as IL-8. A schematic of the amino acid sequence of TyrRS, which is comprised of 3 domains: the Rossmann fold catalytic domain (yellow, residues 1-230), the anticodon recognition domain (green, residues 231-364) and the C-terminal domain (purple, residues 364-528) is shown in the Top Panel of FIG. 3. The first two domains form the active core enzyme, which is called mini TyrRS (residues 1-364). The recently solved tertiary structure of mini-TyrRS reveals a hydrogen-bonding network around the ELR motif, which tethers the anticodon recognition and active site domains of the protein (see FIG. 3, Bottom Panel). There are two hydrogen bonding interactions between side chain of R93 of the ELR motif and main chain A340 of the anticodon recognition domain, which tether the $\alpha 5$ coil to the $\alpha 14$ coil. Additionally, stacking interactions between the aromatic ring of Y341 and the main chain G46, create a contact between these domains. Of these four residues, R93, G46 and Y341 are conserved in all eukaryotic TyrRS proteins identified so far. As shown in FIG. 3 (Bottom Panel), the complementarity of the surface electrostatic potential of each fragment provides evidence for the tether between the $\alpha 5$ coil and the $\alpha 14$ coil. The ELR motif (on helix $\alpha 5$) is masked by the C-domain, and is exposed when the C-domain is removed. For this reason, mini TyrRS is active, whereas the full-length TyrRS is inactive for angiogenesis. The Tyr341 residue (from the anticodon recognition domain on helix a 14) interacts with the ELR, and plays an important role in tethering C-domain to block the ELR. The A340 is also highly conserved, being replaced only by another small amino acid, glycine, in S. cerevisiae.

Two independent methods were used to demonstrate the three-dimensional structure opening of TyrRS by the Y341A mutation. The first method was Small Angel X-ray Scattering (SAXS). When the wavelength of electromagnetic radiation is on the same length scale as that of a sample particle, the particle will scatter the radiation. Detection and analysis of this scattering pattern can yield valuable information about the size, shape, and internal structure of the particle. The SAXS technique is a powerful technique to detect overall conformational change of macromolecules (like proteins) in solution. From the scattering curves measured with both the wild type human TyrRS and the Y341A mutation, the electron pair distance distribution function for each sample was calculated (FIG. 5). Values for the Radius of Gyration ($R_g$) and Maximum distance ($D_{max}$) were subsequently derived from the distribution functions, P(r).

FIG. 4 shows the hydrogen bond tether between R93 and Y341. Disruption of the hydrogen bond tether opens up the tertiary structure and exposes the ELR motif. Small angle X-ray scattering studies on wild-type human TyrRS and a variant in which Y341 has been replaced by an alanine (TyrRS-Y341A) provides direct evidence for such opening (see FIG. 5). The X-ray scattering studies showed that the electron pair distance distribution broadened in the variant relative to the wild-type protein. TyrRS Y341A has an $R_g$ of about 4 Angstroms larger than those of the wild type TyrRS, and a $D_{max}$ about 20 Angstroms larger. This demonstrates that TyrRS Y341A has a more open and extended conformation relative to wild-type TyrRS.

Additional support for an open structure in TyrRS-Y341A relative to wild-type human TyrRS was obtained from digestion studies using plasmin and elastase. Proteases generally cleave proteins at flexible loop regions, where there are no defined secondary structures like alpha helices or beta strands. The presence of structural opening to expose the ELR motif associated with the Y341A mutation was confirmed by the additional cleavage fragments that were observed as a result of additional cleavage site(s) on the more relaxed, open structure. Using both plasmin and leukocyte elastase, additional cleavage sites on the Y341A mutation were observed, relative to the wild type TyrRS. The observed additional cleavage sites were L333, K334 and A337, which are all located on helix alpha 14 of the anticodon recognition domain, close to the mutation site 341. This confirmed that in Y341A mutation, alpha 14 is relaxed and presents itself as a flexible loop, no longer tethered to the ELR region. FIG. 6 schematically illustrates the opening effect of the Y341A mutation on the overall tertiary structure of human TyrRS.

The Y341A mutation conferred angiogenic activity onto the full-length TyrRS. Y341 is an ideal target for mutation, given its conservation among eucaryotes and its involvement in the tertiary structural stability in the region around the ELR motif. This residue was mutated to alanine in full-length TyrRS and mini-TyrRS to determine the extent to which disruption of the tether alters cytokine and enzymatic activities. Cytokine activity was tested in the chick chorioallantoic membrane (CAM) and the Matrigel assays for angiogenesis.

The inclusion of a Y341A mutation in mini-TyrRS produced no observable effect on its activity in the CAM assay—angiogenesis was promoted by both the normal polypeptide and the variant. Full-length, wild-type human TyrRS is inactive in this assay. However, mutation of Y341 of human TyrRS to an alanine (i.e., TyrRS-Y341A) converted this enzyme into a pro-angiogenic cytokine. To confirm the results seen in the CAM assay, the polypeptides were also tested in the mouse Matrigel plug model. In this assay, a collagen plug containing PBS or other protein was injected subcutaneously. When there is a pro-angiogenic factor within the plug, blood vessels perfuse into the plug. Upon injection of a fluorescent endothelial-cell binding lectin, the blood vessel density in each plug can be quantified by spectrophotometric analysis. In this model, VEGF and mini-TyrRS were both positive for angiogenic activity. Wild-type TyrRS was inactive, with levels of angiogenesis similar to PBS. In contrast, TyrRS-Y341A induced angiogenesis. These data independently confirmed the CAM assay results.

The TyrRS variant having the Y341A mutation caused a marked increase in the vascularization of the area of the CAM membrane containing the implant while neither the wild-type polypeptide or PBS induced a response (polypeptides were applied at a concentration of 1 µM in a nylon mesh-imbedded collagen implant).

Figure 7:
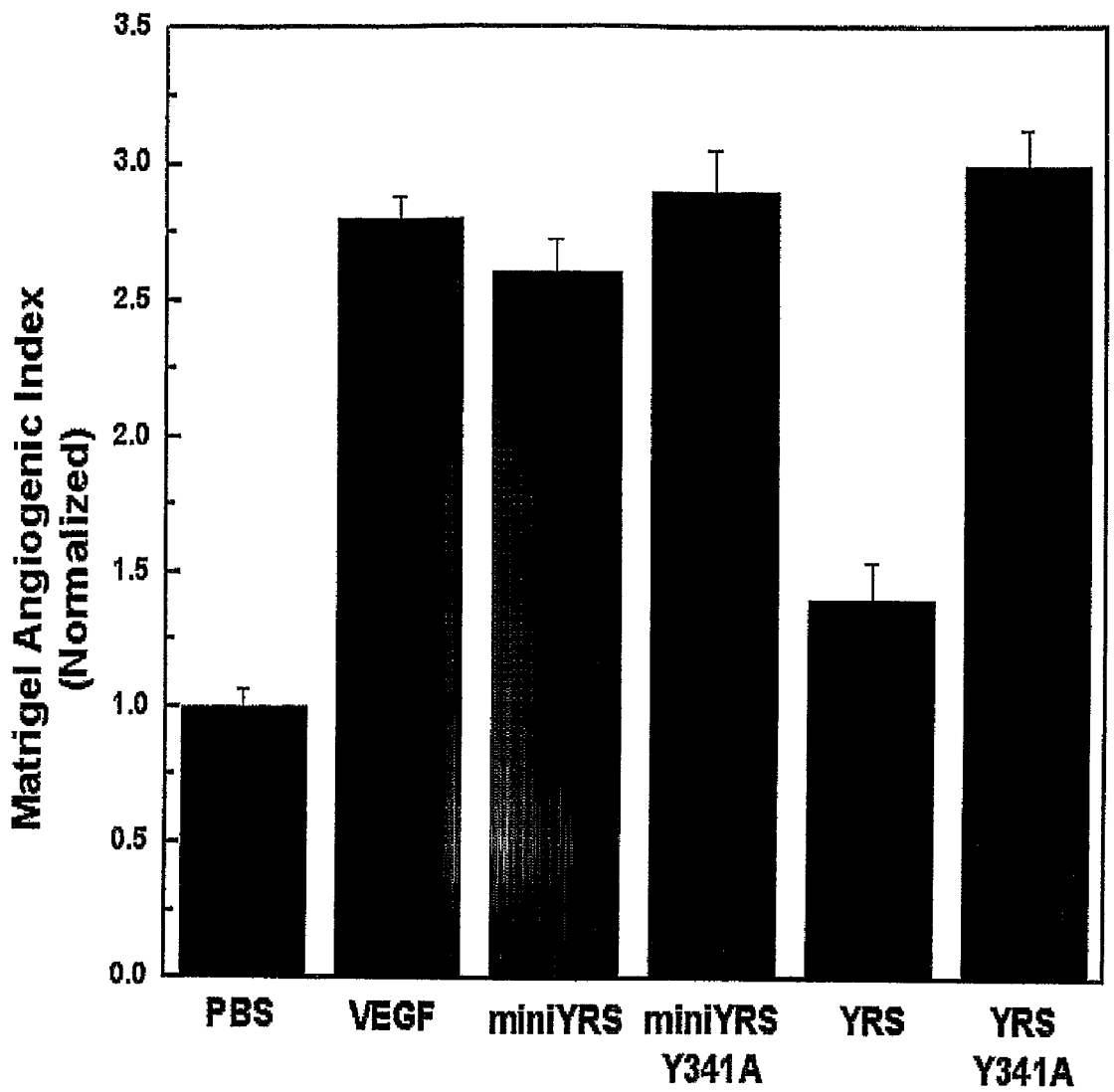
FIG. 7 illustrates the activity of TyrRS-Y341A in the mouse Matrigel angiogenesis model. Mice received a 400 μL subcutaneous injection of growth factor-reduced Matrigel alone or mixed with 250 nM TyrRS proteins. Human $VEGF_{165}$ (20 nM) was used as a positive control. Following a five-day incubation, mice were intravenously injected with fluorescein-labeled endothelial binding lectin *Griffonia (Bandeiraea) Sinplicifolia* I, isolectin B4. The plugs were excised, solubilized, and assessed for fluorescein content by spectrometry. The opened-up TyrRS Y341A variant was observed to have increased angiogenesis activity relative to wild-type TyrRS.

FIG. 7 further characterizes the in vivo activity of the TyrRS polypeptides in the mouse Matrigel plug assay. Mice were administered a 400 µL subcutaneous injection of growth factor-reduced Matrigel alone or mixed with 250 nM protein. Following a five-day incubation, the plugs are removed and assessed for the presence of blood vessels. $VEGF_{165}$ (20 nM) was used as a positive control. As previously reported, mini-TyrRS promoted an angiogenic response in this assay. The mutation of Y341 to alanine in mini-TyrRS (i.e., mini-TyrRS-Y341A) did not affect this response. However, when the Y341A mutation is made in the full-length TyrRS, a 2-fold increase in angiogenic response was noted as compared to the wild-type TyrRS.

Figure 8:
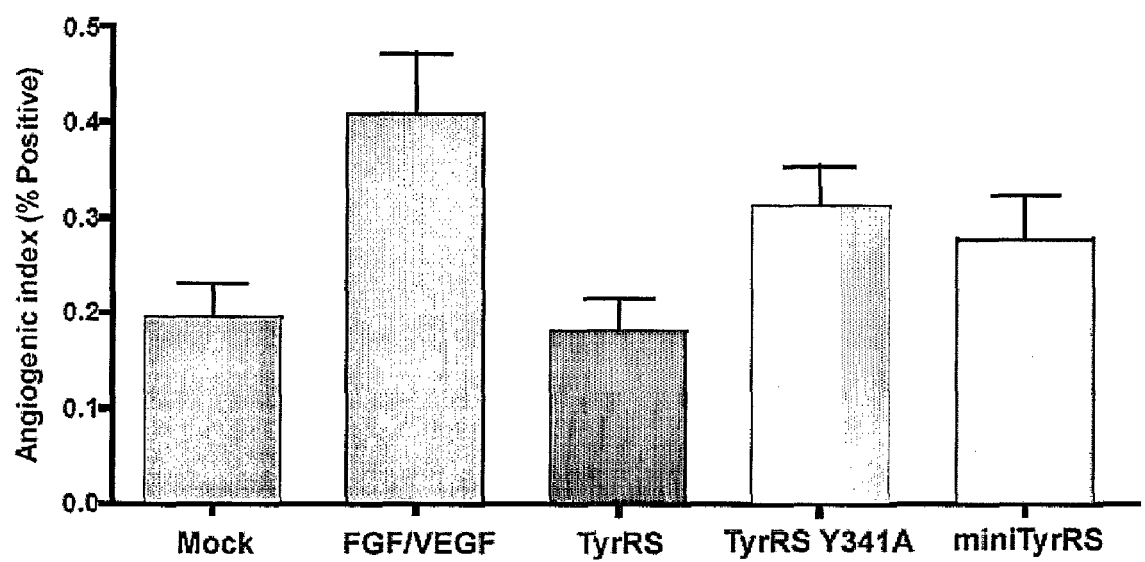
FIG. 8 illustrates the activity of human TyrRS and TyrRS-Y341A in the chick chorioallantoic membrane assay. Angiogenic activity of TyrRS proteins was tested in vivo with the chick chorioallantoic membrane assay. TyrRS variants (1 μM), a positive control consisting of a combination of VEGF and bFGF, as well as a negative control consisting of buffer alone, were applied to the CAM in a nylon mesh-imbedded collagen onplant.

The Y341A mutation inactivated the ability of TyrRS to activate tyrosine. Amino acid activation was assessed by measuring the tyrosine-dependent ATP-PPi exchange reaction. As shown in FIG. 8, the Y341A point mutation knocks out the ability of the full-length TyrRS, as well as the mini-TyrRS, to form the tyrosyl adenylate. Thus, the structural elements that are involved in aminoacylation of tRNA are different from those involved in cytokine function.

Figure 9:
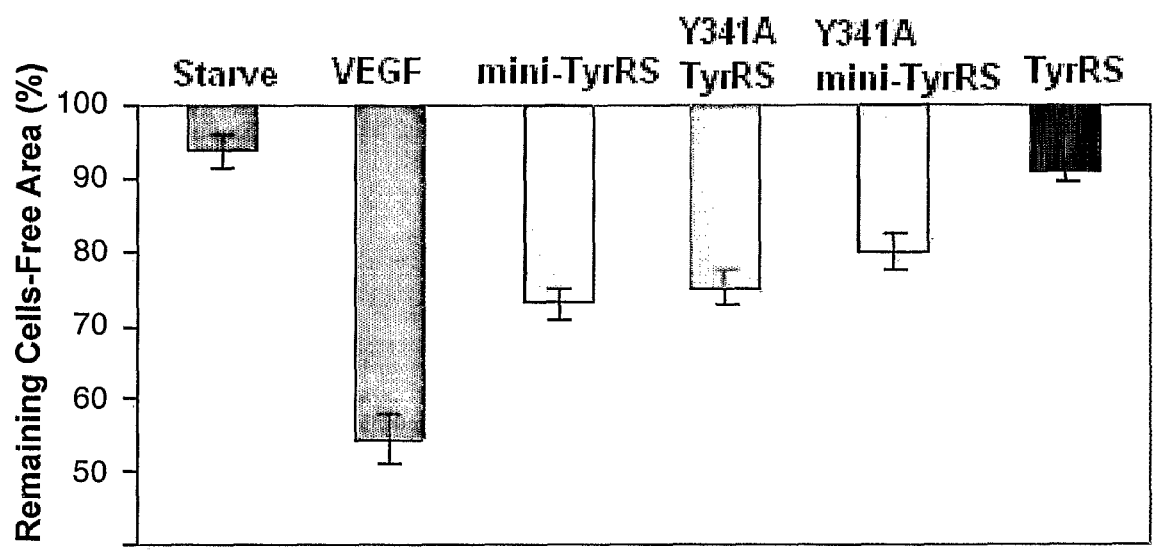
FIG. 9 shows a graph of the percentage area (vertical axis) of the remaining cells-free area compared to the area of the initial wound in wounded endothelial cell cultures treated with TyrRS variants of the invention and control treatments.

An endothelial cell migration assay was used to assess the ability of the TyrRS variants of the invention to stimulate endothelial cell migration, which is associated with wound healing. Human umbilical vein endothelial cells (HUVECs) were plated in EGM media containing 10% FBS and grown to confluent monolayers. The cells were starved in media containing no FBS and then wounded across the well with a pipette tip. The wounded layers were washed with serum-free media to remove cell debris and the cells were allowed to migrate in the presence and absence of TyrRS variants and control factors. Images of the cell-free wound area were taken at 0 and 6 hours post wounding and analyzed using an image analysis software (NIH ImageJ, version 1.33). Endothelial cell migration was calculated as the percentage of the remaining cell-free area compared to the area of the initial wound, from which the % area closed for each condition was determined. FIG. 9 shows a graph of the percentage (vertical axis) of the remaining cell-free area compared to the area of the initial wound in wounded endothelial cell cultures treated with TyrRS variants of the invention and control treatments. A relatively smaller percentage of cell-free area indicates improved endothelial cell migration and wound healing. As shown in FIG. 9, the TyrRS variants of the invention stimulated endothelial cell migration to an extent comparable to miniTyrRS, and to a greater extent than wild-type TyrRS.

Numerous variations and modifications of the embodiments described above may be effected without departing from the spirit and scope of the novel features of the invention. No limitations with respect to the specific embodiments illustrated herein are intended or should be inferred.

---

What is claimed is:

1. An isolated tyrosyl tRNA synthetase (TyrRS) polypeptide variant comprising the amino acid residue sequence of SEQ ID NO: 4 or a fragment thereof, wherein the fragment of SEQ ID NO: 4 comprises at least all of residues 1 through 364 of SEQ ID NO: 4, and wherein residue X at position 341 of SEQ ID NO: 4 is selected from the group consisting of a glycine residue, an alanine residue, a valine residue, a leucine residue, an isoleucine residue, a methionine residue, and a proline residue.

2. The TyrRS polypeptide variant of claim 1 wherein residue X at position 341 of SEQ ID NO: 4 is an amino acid residue selected from the group consisting of a glycine residue, an alanine residue, and a proline residue.

3. The TyrRS polypeptide variant of claim 1 wherein residue X at position 341 of SEQ ID NO: 4 is an alanine residue.

4. An isolated tyrosyl tRNA synthetase (TyrRS) polypeptide variant consisting of the amino acid residue sequence of SEQ ID NO: 4, wherein residue X at position 341 of SEQ ID NO: 4 is selected from the group consisting of a glycine residue, an alanine residue, a phenylalanine residue, a valine residue, a leucine residue, an isoleucine residue, a methionine residue, and a proline residue.

5. The TyrRS polypeptide variant of claim 4 wherein residue X at position 341 of SEQ ID NO: 4 is selected from the group consisting of a glycine residue, an alanine residue, and a proline residue.

6. The TyrRS polypeptide variant of claim 4 wherein residue X at position 341 of SEQ ID NO: 4 is an alanine residue.

* * * * *

UNITED STATES PATENT AND TRADEMARK OFFICE
CERTIFICATE OF CORRECTION

PATENT NO. : 8,026,088 B2
APPLICATION NO. : 12/085884
DATED : September 27, 2011
INVENTOR(S) : Xiang-Lei Yang et al.

Page 1 of 1

It is certified that error appears in the above-identified patent and that said Letters Patent is hereby corrected as shown below:

In the Specification

Column 1, Lines 12-17, the paragraph STATEMENT OF GOVERNMENT INTEREST should be changed to:
-- STATEMENT OF GOVERNMENT LICENSE RIGHTS
This invention was made with government support under grant number CA092577 awarded by the National Institutes of Health. The government has certain rights in the invention. --

Signed and Sealed this
Seventh Day of April, 2020

Andrei Iancu
*Director of the United States Patent and Trademark Office*